United States Patent
Ingmanson et al.

(10) Patent No.: US 10,117,654 B2
(45) Date of Patent: Nov. 6, 2018

(54) METHOD OF EMERGENCY RETRACTION FOR ELECTRO-MECHANICAL SURGICAL DEVICES AND SYSTEMS

(71) Applicant: Covidien LP, Mansfield, MA (US)

(72) Inventors: Michael Ingmanson, Stratford, CT (US); Josh Snow, Clinton, CT (US); Thomas Wingardner, North Haven, CT (US); David McCuen, Stratford, CT (US); Philip Irka, Northford, CT (US)

(73) Assignee: Covidien LP, Mansfield, MA (US)

( * ) Notice: Subject to any disclaimer, the term of this patent is extended or adjusted under 35 U.S.C. 154(b) by 622 days.

(21) Appl. No.: 14/285,856

(22) Filed: May 23, 2014

(65) Prior Publication Data
US 2014/0367446 A1    Dec. 18, 2014

Related U.S. Application Data

(60) Provisional application No. 61/836,181, filed on Jun. 18, 2013.

(51) Int. Cl.
*A61B 17/00* (2006.01)
*A61B 17/072* (2006.01)
*A61B 90/00* (2016.01)

(52) U.S. Cl.
CPC ........ *A61B 17/07207* (2013.01); *A61B 90/03* (2016.02); *A61B 2017/00017* (2013.01); *A61B 2017/0046* (2013.01); *A61B 2017/00398* (2013.01); *A61B 2017/00473* (2013.01); *A61B 2017/00477* (2013.01); *A61B 2017/00734* (2013.01); *A61B 2090/0812* (2016.02)

(58) Field of Classification Search
CPC ............... A61B 17/068; A61B 17/072; A61B 17/07207; A61B 2017/00734; A61B 2017/00017; A61B 90/03
USPC ......... 227/175.1, 175.2, 175.3, 175.4, 176.1, 227/177.7, 178.1, 179.1
See application file for complete search history.

(56) References Cited

U.S. PATENT DOCUMENTS

| | | | |
|---|---|---|---|
| 5,071,052 A | 12/1991 | Rodak et al. | |
| 5,306,234 A | 4/1994 | Johnson | |

(Continued)

FOREIGN PATENT DOCUMENTS

| | | |
|---|---|---|
| CN | 101401736 A | 4/2009 |
| EP | 2044890 A1 | 4/2009 |

(Continued)

OTHER PUBLICATIONS

European Office Action corresponding to counterpart Int'l Appln. EP 14 17 2681.0, dated May 13, 2016.

(Continued)

*Primary Examiner* — Gloria R Weeks

(57) ABSTRACT

The present disclosure relates to an electromechanical surgical system and methods for use thereof including a surgical instrument having a controller, and an end effector selectively and removably connectable to the surgical instrument, wherein the controller enters an emergency retraction mode when at least one input element of the surgical system is incapable of providing control signals to the controller to operate a motor, wherein the emergency retraction mode activates the motor to withdraw a drive assembly from any advanced position thereof.

17 Claims, 12 Drawing Sheets

(56) References Cited

U.S. PATENT DOCUMENTS

| | | | |
|---|---|---|---|
| 5,360,405 A * | 11/1994 | Yoon | A61B 17/3417 604/157 |
| 5,397,046 A | 3/1995 | Savage et al. | |
| 5,413,267 A | 5/1995 | Solyntjes et al. | |
| 5,415,335 A | 5/1995 | Knodell, Jr. | |
| 5,715,988 A | 2/1998 | Palmer | |
| 5,718,359 A | 2/1998 | Palmer et al. | |
| 6,109,500 A | 8/2000 | Alli et al. | |
| 6,254,642 B1 | 7/2001 | Taylor | |
| 6,264,087 B1 | 7/2001 | Whitman | |
| 6,315,184 B1 | 11/2001 | Whitman | |
| 6,348,061 B1 | 2/2002 | Whitman | |
| 6,443,973 B1 | 9/2002 | Whitman | |
| 6,488,197 B1 | 12/2002 | Whitman | |
| 6,491,201 B1 | 12/2002 | Whitman | |
| 6,505,768 B2 | 1/2003 | Whitman | |
| 6,517,565 B1 | 2/2003 | Whitman et al. | |
| 6,533,157 B1 | 3/2003 | Whitman | |
| 6,681,979 B2 | 1/2004 | Whitman | |
| 6,695,199 B2 | 2/2004 | Whitman | |
| 6,698,643 B2 | 3/2004 | Whitman | |
| 6,716,230 B2 | 4/2004 | Whitman | |
| 6,716,233 B1 | 4/2004 | Whitman | |
| 6,793,652 B1 * | 9/2004 | Whitman | A61B 10/0233 128/898 |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,981,941 B2 | 1/2006 | Whitman et al. | |
| 7,032,798 B2 | 4/2006 | Whitman et al. | |
| 7,077,856 B2 | 7/2006 | Whitman | |
| 7,114,642 B2 | 10/2006 | Whitman | |
| 7,314,472 B2 * | 1/2008 | Jinno | A61B 17/00234 414/2 |
| 7,537,602 B2 | 5/2009 | Whitman | |
| 7,695,485 B2 | 4/2010 | Whitman et al. | |
| 7,743,960 B2 | 6/2010 | Whitman et al. | |
| 7,751,870 B2 | 7/2010 | Whitman | |
| 7,758,613 B2 | 7/2010 | Whitman | |
| 7,770,773 B2 | 8/2010 | Whitman et al. | |
| 7,803,151 B2 | 9/2010 | Whitman | |
| 7,815,092 B2 | 10/2010 | Whitman et al. | |
| 7,845,538 B2 | 12/2010 | Whitman | |
| 7,874,981 B2 | 1/2011 | Whitman et al. | |
| 7,905,897 B2 | 3/2011 | Whitman et al. | |
| 7,918,230 B2 | 4/2011 | Whitman et al. | |
| 7,947,034 B2 | 5/2011 | Whitman | |
| 7,951,071 B2 | 5/2011 | Whitman et al. | |
| 7,963,433 B2 | 6/2011 | Whitman et al. | |
| 7,992,758 B2 | 8/2011 | Whitman et al. | |
| 8,008,598 B2 | 8/2011 | Whitman et al. | |
| 8,012,170 B2 | 9/2011 | Whitman et al. | |
| 8,016,855 B2 | 9/2011 | Whitman et al. | |
| 8,016,858 B2 | 9/2011 | Whitman | |
| 8,021,373 B2 | 9/2011 | Whitman et al. | |
| 8,025,199 B2 | 9/2011 | Whitman et al. | |
| 8,056,786 B2 | 11/2011 | Whitman et al. | |
| 8,056,791 B2 | 11/2011 | Whitman | |
| 8,118,208 B2 | 2/2012 | Whitman | |
| 8,132,704 B2 | 3/2012 | Whitman et al. | |
| 8,171,276 B2 * | 5/2012 | Fried | G06F 8/61 713/2 |
| 8,186,559 B1 | 5/2012 | Whitman | |
| 8,210,413 B2 | 7/2012 | Whitman et al. | |
| 8,229,549 B2 | 7/2012 | Whitman et al. | |
| 8,235,272 B2 | 8/2012 | Nicholas et al. | |
| 8,241,322 B2 | 8/2012 | Whitman et al. | |
| 8,262,560 B2 | 9/2012 | Whitman | |
| 8,272,554 B2 | 9/2012 | Whitman et al. | |
| 8,292,888 B2 | 10/2012 | Whitman | |
| 8,342,379 B2 | 1/2013 | Whitman et al. | |
| 8,353,440 B2 | 1/2013 | Whitman et al. | |
| 8,357,144 B2 | 1/2013 | Whitman et al. | |
| 8,381,828 B2 | 2/2013 | Whitman et al. | |
| 8,444,037 B2 | 5/2013 | Nicholas et al. | |
| 8,454,585 B2 | 6/2013 | Whitman | |
| 8,459,523 B2 | 6/2013 | Whitman | |
| 8,480,703 B2 | 7/2013 | Nicholas et al. | |
| 8,499,992 B2 | 8/2013 | Whitman et al. | |
| 8,512,359 B2 | 8/2013 | Whitman et al. | |
| 8,517,241 B2 | 8/2013 | Nicholas et al. | |
| 8,518,074 B2 | 8/2013 | Whitman et al. | |
| 8,523,890 B2 | 9/2013 | Whitman | |
| 8,540,733 B2 | 9/2013 | Whitman et al. | |
| 8,608,045 B2 * | 12/2013 | Smith | A61B 17/07207 227/175.2 |
| 8,628,467 B2 | 1/2014 | Whitman et al. | |
| 8,636,193 B2 | 1/2014 | Whitman et al. | |
| 8,636,762 B2 | 1/2014 | Whitman et al. | |
| 8,647,258 B2 | 2/2014 | Aranyi et al. | |
| 8,690,913 B2 | 4/2014 | Whitman | |
| 8,740,932 B2 | 6/2014 | Whitman et al. | |
| 8,752,748 B2 | 6/2014 | Whitman et al. | |
| 8,771,169 B2 | 7/2014 | Whitman et al. | |
| 8,806,973 B2 | 8/2014 | Ross et al. | |
| 8,812,086 B2 | 8/2014 | Whitman | |
| 8,814,785 B2 | 8/2014 | Whitman et al. | |
| 8,920,300 B2 * | 12/2014 | Roberts | A61N 5/1001 600/3 |
| 8,967,443 B2 * | 3/2015 | McCuen | A61B 17/07207 227/175.1 |
| 9,675,348 B2 * | 6/2017 | Smith | A61B 17/115 |
| 9,713,473 B2 * | 7/2017 | Smith | A61B 17/072 |
| 2002/0134811 A1 * | 9/2002 | Napier | B24B 23/04 227/131 |
| 2007/0055219 A1 | 3/2007 | Whitman et al. | |
| 2009/0090763 A1 * | 4/2009 | Zemlok | A61B 17/07207 227/175.2 |
| 2009/0314821 A1 | 12/2009 | Racenet | |
| 2010/0030233 A1 | 2/2010 | Whitman et al. | |
| 2010/0324541 A1 | 12/2010 | Whitman | |
| 2011/0121049 A1 | 5/2011 | Malinouskas et al. | |
| 2011/0125138 A1 | 5/2011 | Malinouskas et al. | |
| 2011/0144679 A1 | 6/2011 | Whitman et al. | |
| 2011/0144681 A1 | 6/2011 | Whitman et al. | |
| 2011/0166587 A1 | 7/2011 | Whitman et al. | |
| 2011/0192883 A1 | 8/2011 | Whitman et al. | |
| 2011/0203825 A1 * | 8/2011 | Nishio | A61B 17/1626 173/213 |
| 2011/0257634 A1 | 10/2011 | Whitman et al. | |
| 2011/0257636 A1 | 10/2011 | Whitman et al. | |
| 2011/0290054 A1 | 12/2011 | Whitman et al. | |
| 2011/0290858 A1 | 12/2011 | Whitman et al. | |
| 2012/0089131 A1 * | 4/2012 | Zemlok | A61B 17/07207 606/1 |
| 2012/0119873 A1 * | 5/2012 | Ramsdell | G08C 17/00 340/4.3 |
| 2012/0253329 A1 | 10/2012 | Zemlok et al. | |
| 2012/0310097 A1 | 12/2012 | Whitman et al. | |
| 2012/0310221 A1 * | 12/2012 | Durant | A61B 34/30 606/1 |
| 2012/0310254 A1 * | 12/2012 | Manzo | A61B 34/30 606/130 |
| 2012/0323226 A1 | 12/2012 | Chowaniec et al. | |
| 2013/0035598 A1 | 2/2013 | Whitman | |
| 2013/0082662 A1 * | 4/2013 | Carre | H02J 7/0052 320/134 |
| 2013/0112730 A1 | 5/2013 | Whitman et al. | |
| 2013/0131650 A1 | 5/2013 | Whitman et al. | |
| 2013/0233907 A1 | 9/2013 | Nicholas et al. | |
| 2013/0240596 A1 | 9/2013 | Whitman | |
| 2013/0245704 A1 * | 9/2013 | Koltz | A61B 17/00 606/86 A |
| 2013/0264369 A1 | 10/2013 | Whitman | |
| 2013/0274797 A1 | 10/2013 | Nicholas et al. | |
| 2013/0292452 A1 | 11/2013 | Whitman | |
| 2013/0317486 A1 | 11/2013 | Nicholas et al. | |
| 2013/0324978 A1 | 12/2013 | Nicholas et al. | |
| 2014/0008410 A1 | 1/2014 | Whitman et al. | |
| 2014/0008411 A1 | 1/2014 | Whitman et al. | |
| 2014/0018802 A1 | 1/2014 | Whitman | |

(56) References Cited

U.S. PATENT DOCUMENTS

| | | |
|---|---|---|
| 2014/0025105 A1 | 1/2014 | Whitman et al. |
| 2014/0046354 A1 | 2/2014 | Whitman |
| 2014/0066702 A1 | 3/2014 | Whitman |
| 2014/0103091 A1 | 4/2014 | Whitman et al. |
| 2014/0131416 A1 | 5/2014 | Whitman et al. |
| 2014/0135575 A1 | 5/2014 | Whitman et al. |
| 2014/0175148 A1 | 6/2014 | Whitman |
| 2014/0180000 A1 | 6/2014 | Whitman |
| 2014/0277017 A1* | 9/2014 | Leimbach ........ A61B 17/07207 606/167 |
| 2014/0367445 A1* | 12/2014 | Ingmanson ...... A61B 17/07207 227/175.2 |
| 2014/0367446 A1* | 12/2014 | Ingmanson ...... A61B 17/07207 227/175.2 |
| 2015/0053739 A1* | 2/2015 | Morgan ............... A61B 17/068 227/175.2 |
| 2015/0122870 A1* | 5/2015 | Zemlok ................... H02P 7/29 227/176.1 |
| 2015/0209035 A1* | 7/2015 | Zemlok ................ G01D 18/008 73/1.01 |
| 2015/0272581 A1* | 10/2015 | Leimbach ........ A61B 17/07207 227/175.2 |
| 2016/0324588 A1* | 11/2016 | Durant ................... A61B 34/71 |
| 2017/0135749 A1* | 5/2017 | Cagle ................. A61B 18/1445 |
| 2017/0181804 A1* | 6/2017 | Manzo ................... A61B 34/71 |
| 2017/0231623 A1* | 8/2017 | Shelton, IV ......... A61B 17/068 227/176.1 |
| 2017/0231627 A1* | 8/2017 | Shelton, IV ..... A61B 17/07207 227/180.1 |
| 2017/0231628 A1* | 8/2017 | Shelton, IV ..... A61B 17/07207 227/180.1 |
| 2017/0296173 A1* | 10/2017 | Shelton, IV ......... A61B 17/068 |

FOREIGN PATENT DOCUMENTS

| | | |
|---|---|---|
| EP | 2510891 | 10/2012 |
| EP | 2586382 A2 | 5/2013 |
| JP | 2006325940 A | 12/2006 |
| WO | 02/43571 | 6/2002 |
| WO | 0243571 A2 | 6/2002 |
| WO | 2012/166807 A1 | 12/2012 |
| WO | 2012166815 A1 | 12/2012 |

OTHER PUBLICATIONS

Extended European Search Report corresponding to EP 14 17 2681.0, completed Nov. 12, 2014 and dated Nov. 24, 2014; (7 pp).

Chinese Office Action issued in Appl. No. CN201410273504.0 dated Jun. 22, 2017.

Australian Examination Report dated Mar. 16, 2018 issued in corresponding Australian Application No. 2014203037.

Japanese Office Action dated Mar. 15, 2018 issued in corresponding Japanese Application No. 2014-124290.

\* cited by examiner

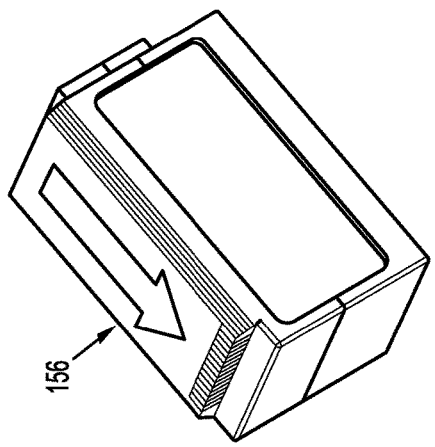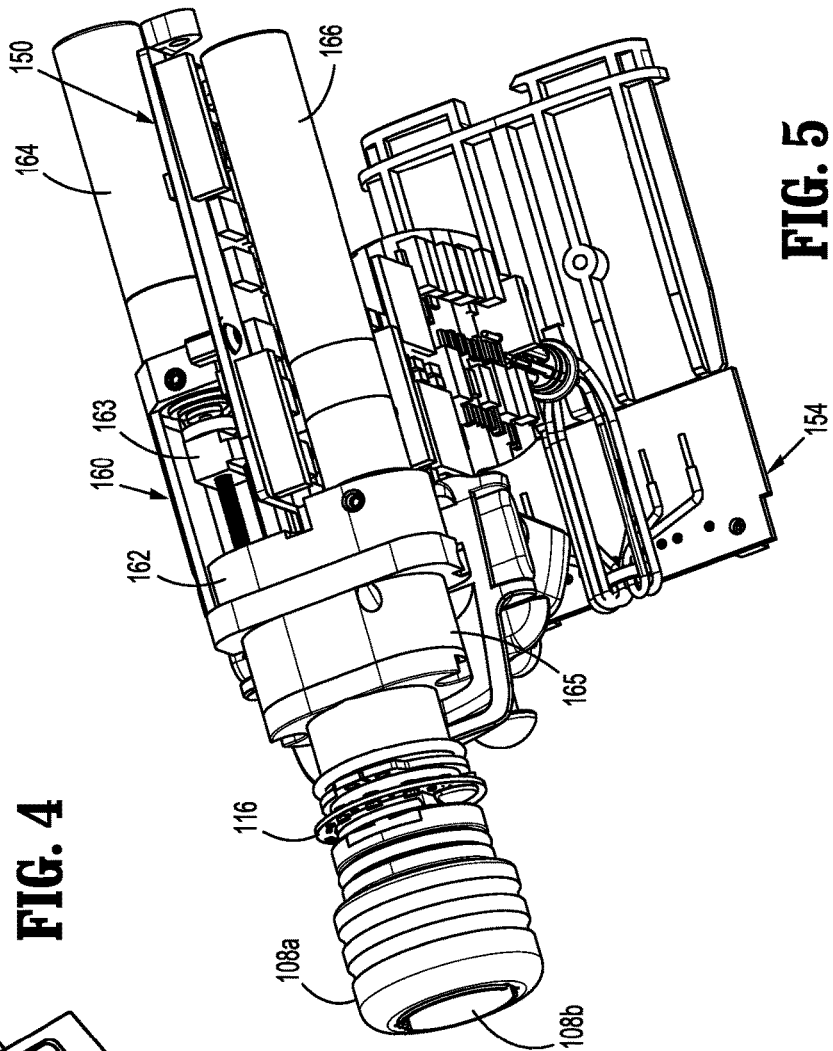
FIG. 4
FIG. 5

METHOD OF EMERGENCY RETRACTION FOR ELECTRO-MECHANICAL SURGICAL DEVICES AND SYSTEMS

CROSS-REFERENCE TO RELATED APPLICATIONS

This application claims the benefit of and priority to U.S. Provisional Patent Application No. 61/836,181, filed Jun. 18, 2013, the entire disclosure of which is incorporated by reference herein.

BACKGROUND

1. Technical Field

The present disclosure relates to surgical devices and/or systems, and more specifically, to electromechanical robotic and/or hand-held powered surgical devices and/or systems including an emergency retraction algorithm.

2. Background of Related Art

A number of surgical device manufacturers have developed product lines with proprietary drive systems for operating and/or manipulating electromechanical surgical devices. In many instances the electromechanical surgical devices include a reusable handle assembly, and disposable or single use end effectors. The end effectors are selectively connected to the handle assembly prior to use and then disconnected from the handle assembly following use in order to be disposed of or in some instances sterilized for re-use.

Many of these electromechanical surgical devices include complex drive components that utilize a variety of user interfaces that accept user inputs (e.g., controls, buttons, toggles, screens, switches, etc.) for controlling the devices as well as provide feedback to the user. To prevent actuation of drive mechanisms beyond mechanical limits, various switches and sensors are used to detect operational state of the surgical devices. Inclusion of multiple switches and/or sensors in the devices as well as end effectors presents various problems. In addition, cost or other considerations prevent the use of such devices. Accordingly, there is a need for systems and apparatuses having safety mechanisms that can detect mechanical limits without relying on multiple mechanical limit sensors and/or switches disposed throughout the surgical device.

Robotic systems for performing minimally invasive surgery are also known. In WO 2000/51486, the entire contents of which are incorporated herein by reference, a system is disclosed in which surgical instruments are remotely controlled.

Additionally, electromechanical surgical devices offer distinct advantages over purely mechanical devices. However, such electromechanical surgical devices are susceptible to previously unconsidered failure modes. For example, one such failure mode is the malfunction of any one or all of the user inputs, identified above, or otherwise contemplated or implemented. Such a failure could result in the electromechanical surgical device being rendered non-operational at a time when at least minimum levels of functionality are critical.

Accordingly, a need exists for methods, in the form of algorithms, and associated software and hardware implementing the methods which reduce risks associated with such failures of electromechanical surgical devices.

SUMMARY

The present disclosure relates to electromechanical robotic and/or hand-held powered surgical devices and/or systems including an emergency retraction algorithm.

According to an aspect of the present disclosure, an electromechanical surgical system is provided comprises a hand-held surgical instrument including a handle housing; a motor disposed within the handle housing; a controller disposed within the handle housing and being in electrical communication with the motor; a battery selectively, removably insertable into the handle housing and being in electrical communication with at least one of the motor and the controller when disposed within the handle housing; and at least one input element supported on the handle housing and actuatable by a user to send control signals to the controller to operate the motor. The surgical system also comprises an end effector selectively and removably connectable to the surgical instrument, the end effector including a jaw assembly having a staple cartridge containing a plurality of staples and an anvil to form the plurality of staples upon firing; and a drive assembly at least partially located within the jaw assembly and operatively connectable to the motor when the end effector is connected to the surgical instrument for actuation by the motor. The controller is configured to enter an emergency retraction mode when the at least one input element is incapable of providing control signals to the controller to operate the motor, wherein the emergency retraction mode activates the motor to withdraw the drive assembly from any advanced position thereof.

The emergency retraction mode may be entered upon a removal and a re-insertion of the battery into the handle housing.

Alternatively, the emergency retraction mode may be entered by activating a switch, optionally protected by additional switch sequences or interlocks or by entering a specialized sequence of control buttons normally used for other purposes.

The emergency retraction mode may also be actuated by encountering an end effector with a readable memory indicating the end effector was previously used or associated with a previous an electromechanical surgical system.

In use, during the emergency retraction mode, the controller may undergo a re-boot, whereby the controller detects that the end effector is connected to the surgical instrument.

In the emergency retraction mode, the drive assembly may be automatically retracted.

In use, retraction of the drive assembly to a fully retracted position, may open the jaw assembly.

In use, in the emergency refraction mode the controller may disable all remaining functions of the surgical system.

The emergency retraction mode may be entered upon a removal of the battery into the handle housing, then a pressing and holding of a safety button, and then a re-insertion of the battery into the handle housing, wherein the safety button is supported on the handle housing.

In use, during the emergency retraction mode, the controller may undergo a re-boot, whereby the controller detects that the end effector is connected to the surgical instrument.

In use, following retraction of the drive assembly, when the safety button is released, the controller may not automatically re-advance the drive assembly.

In use, following a release of the safety button, and following a re-pressing and holding of the safety button, in the emergency retraction mode, the controller may activate the motor to re-close the jaw assembly.

In use, in the emergency refraction mode the controller may disable all remaining functions of the surgical system with the exception of an articulation function.

In use, in the emergency retraction mode, the surgical instrument may be operable to articulate the end effector.

According to another aspect of the present disclosure, a method for controlling an electromechanical surgical system that includes a hand-held surgical instrument selectively and removably supporting an end effector, is provided. The surgical instrument includes a motor, a controller in electrical communication with the motor, a battery in electrical communication with at least one of the motor and the controller, and at least one input element actuatable by a user to send control signals to the controller to operate the motor; and wherein the end effector includes a jaw assembly, a drive assembly at least partially located within the jaw assembly and operatively connectable to the motor when the end effector is connected to the surgical instrument for actuation by the motor.

The method comprises the steps of monitoring the at least one input element; when the at least one input element is incapable of providing control signals to the controller, entering an emergency retraction mode; activating the motor to withdraw the drive assembly from any advanced position thereof.

The method may further comprise the step of entering the emergency retraction mode upon a removal and a re-insertion of the battery into the surgical instrument.

The method may further comprise the steps of wherein during the emergency retraction mode, undergoing a re-boot of the controller; and detecting, by the controller, that the end effector is connected to the surgical instrument.

The method may further comprise the step of retracting the drive assembly automatically while in the emergency retraction mode.

The method may further comprise the step of opening the jaw assembly concomitantly with the retraction of the drive assembly to a fully retracted position.

The method may further comprise step of the controller disabling all remaining functions of the surgical system when in the emergency retraction mode.

The method may further comprise the steps of entering the emergency retraction mode upon a removal and a re-insertion of the battery into the surgical instrument; thereafter, pressing and holding of a safety button supported on the surgical instrument; and thereafter, re-inserting the battery into the surgical instrument.

The method may further comprise the steps of wherein during the emergency retraction mode, undergoing a re-boot of the controller; and detecting, by the controller, that the end effector is connected to the surgical instrument.

The method may further comprise the step of retracting the drive assembly automatically while in the emergency retraction mode.

The method may further comprise the step of opening the jaw assembly concomitantly with the retraction of the drive assembly to a fully retracted position.

The method may further comprise the step of, following retraction of the drive assembly, and following a release of the safety button, the controller does not automatically re-advance the drive assembly.

The method may further comprise the step of, following a release of the safety button, and following a re-pressing and holding of the safety button, in the emergency retraction mode, the controller activates the motor to re-close the jaw assembly.

The method may further comprise the step of, while in the emergency retraction mode, disabling all remaining functions of the surgical system, by the controller, with the exception of an articulation function.

The method may further comprise the step of articulating the end effector while in the emergency retraction mode.

BRIEF DESCRIPTION OF THE DRAWINGS

Embodiments of the present disclosure are described herein with reference to the accompanying drawings, wherein:

FIG. 4 is a perspective view of a battery of the surgical instrument of FIG. 1, according to the present disclosure;

FIG. 5 is a top, partially-disassembled view of the surgical instrument of FIG. 1, according to the present disclosure;

DETAILED DESCRIPTION OF EMBODIMENTS

Figure 1:
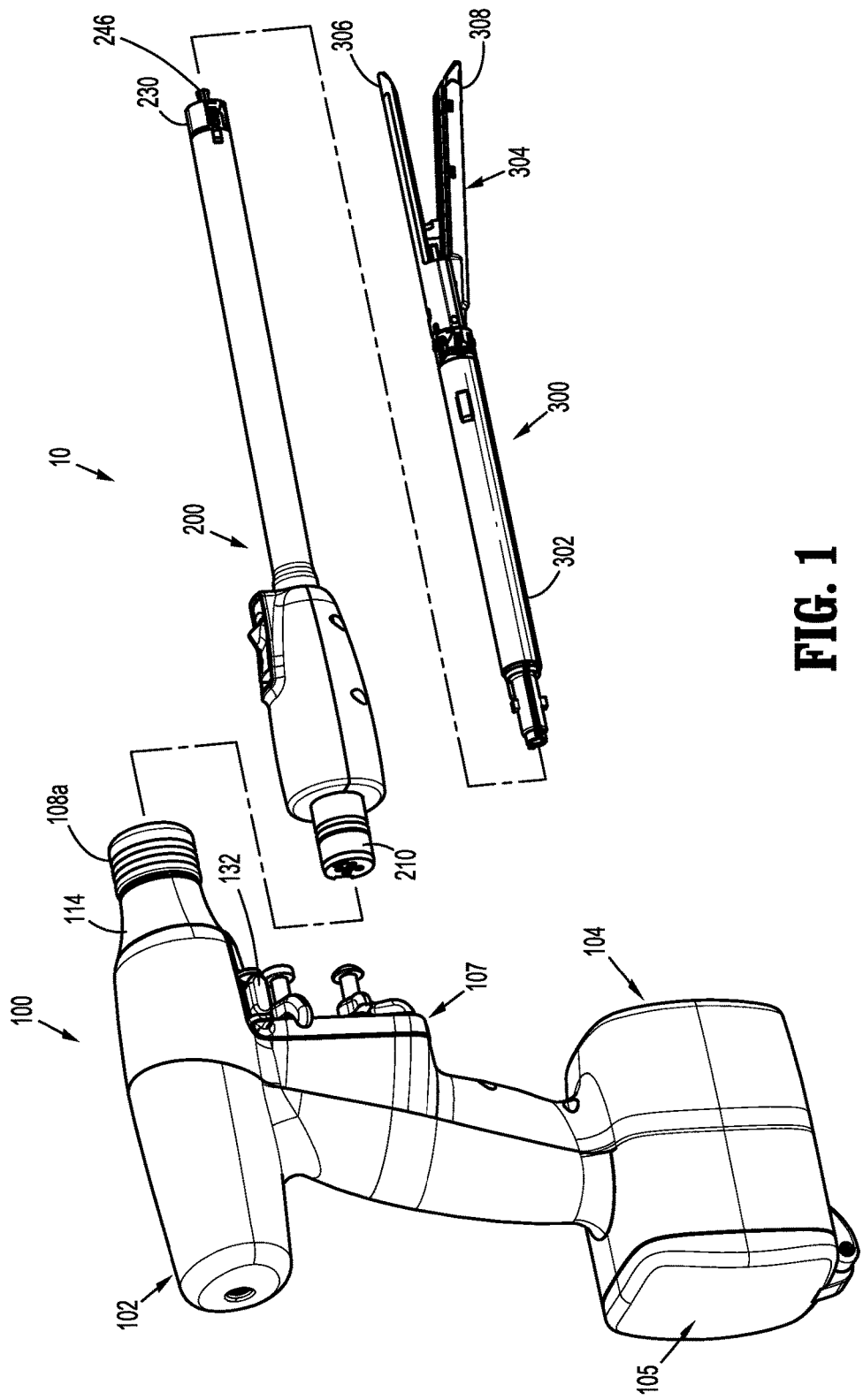
FIG. 1 is a perspective, disassembled view of an electromechanical surgical system including a surgical instrument, an adapter, and an end effector, according to the present disclosure.

Embodiments of the presently disclosed electromechanical surgical system, surgical devices, and adapter assemblies for surgical devices and/or handle assemblies are described in detail with reference to the drawings, in which like reference numerals designate identical or corresponding elements in each of the several views. As used herein the term "distal" refers to that portion of the electromechanical surgical system, the adapter assembly or the surgical device, or components thereof, farther from the user, while the term "proximal" refers to that portion of the electromechanical surgical system, the adapter assembly or the surgical device, or components thereof, closer to the user.

A surgical system, in accordance with an embodiment of the present disclosure, is generally designated as 10, and is in the form of a powered hand held electromechanical instrument configured for selective attachment thereto of a plurality of different end effectors that are each configured for actuation and manipulation by the powered hand held electromechanical surgical instrument.

As illustrated in FIG. 1, surgical instrument 100 is configured for selective connection with an adapter 200, and, in turn, adapter 200 is configured for selective connection with an end effector or single use loading unit 300.

Figure 2:
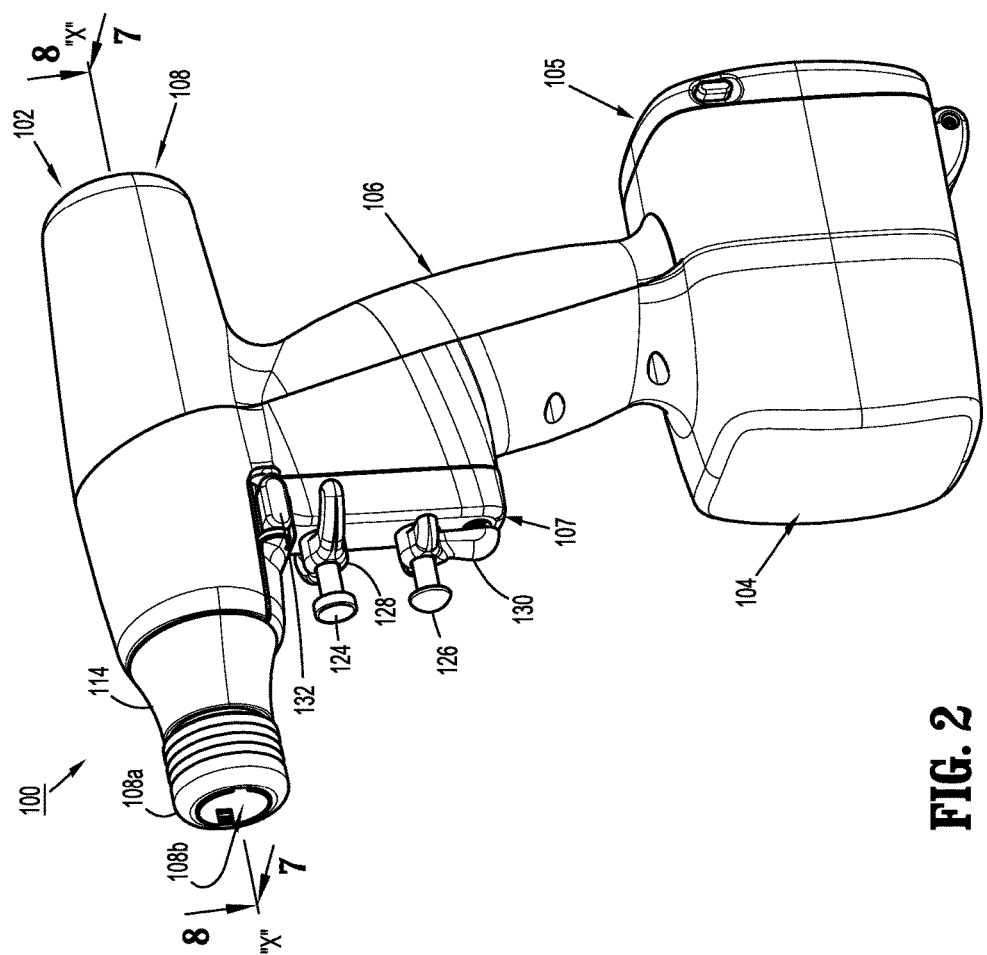
FIG. 2 is a perspective view of the surgical instrument of FIG. 1, according to the present disclosure.
Figure 3:
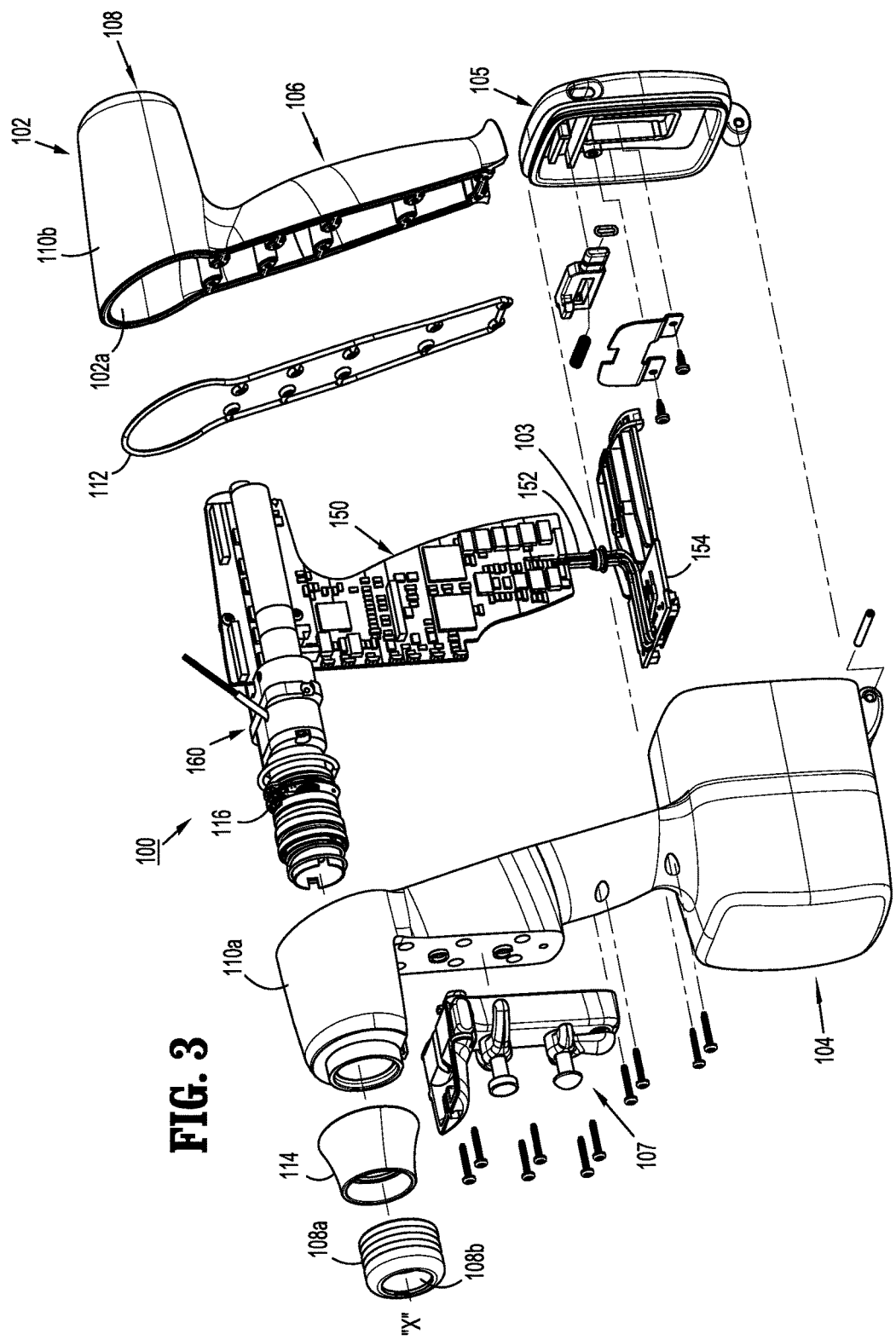
FIG. 3 is perspective, exploded view of the surgical instrument of FIG. 1, according to the present disclosure.

As illustrated in FIGS. 1-3, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIGS. 2 and 3. Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Lower housing portion 104 of surgical instrument 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 may be a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 (see FIGS. 1 and 9) relative to proximal body portion 302 of end effector 300, to rotate end effector 300 about a longitudinal axis "X" (see FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
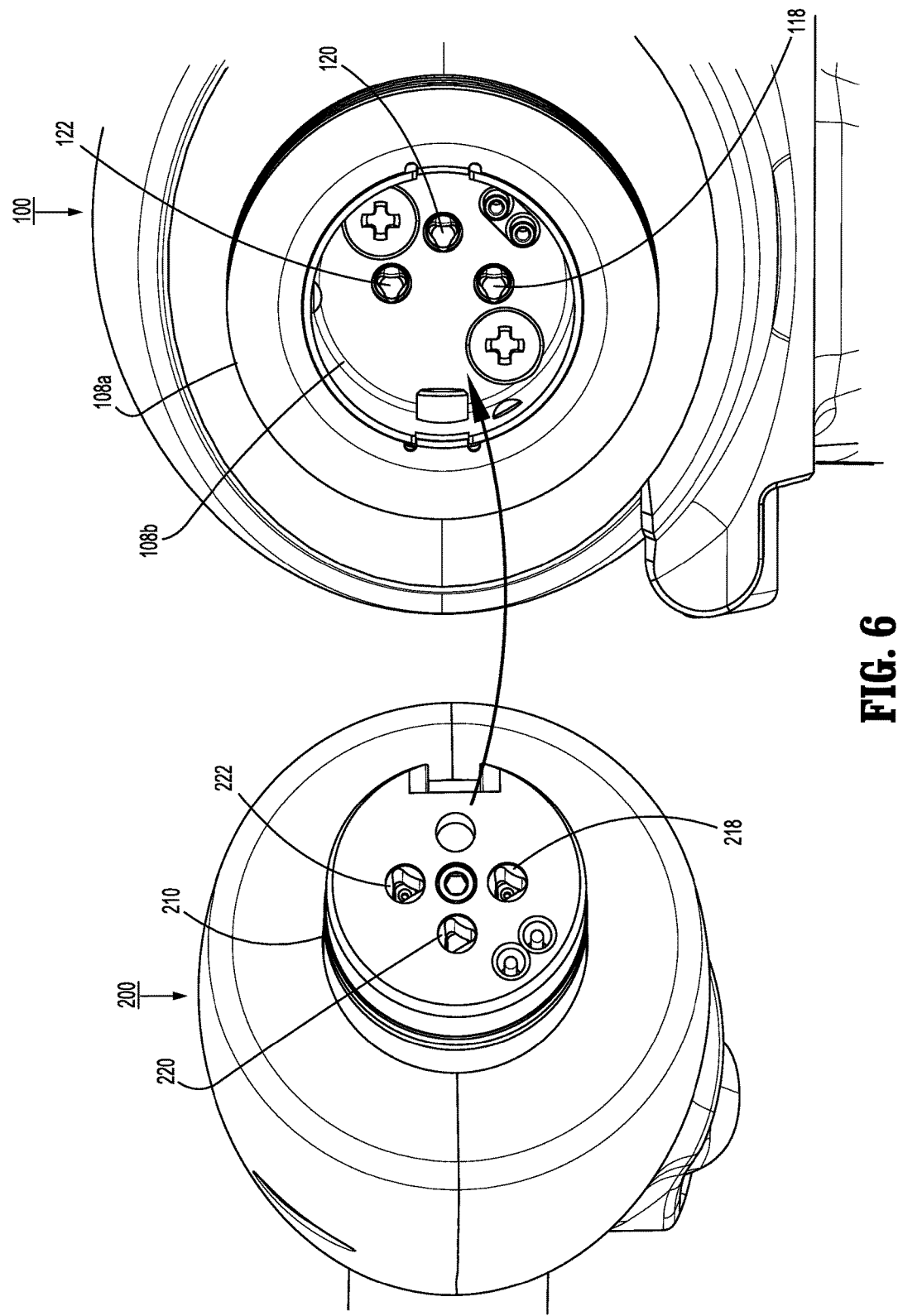
FIG. 6 is a front, perspective view of the surgical instrument of FIG. 1 with the adapter separated therefrom, according to the present disclosure.
Figure 7:
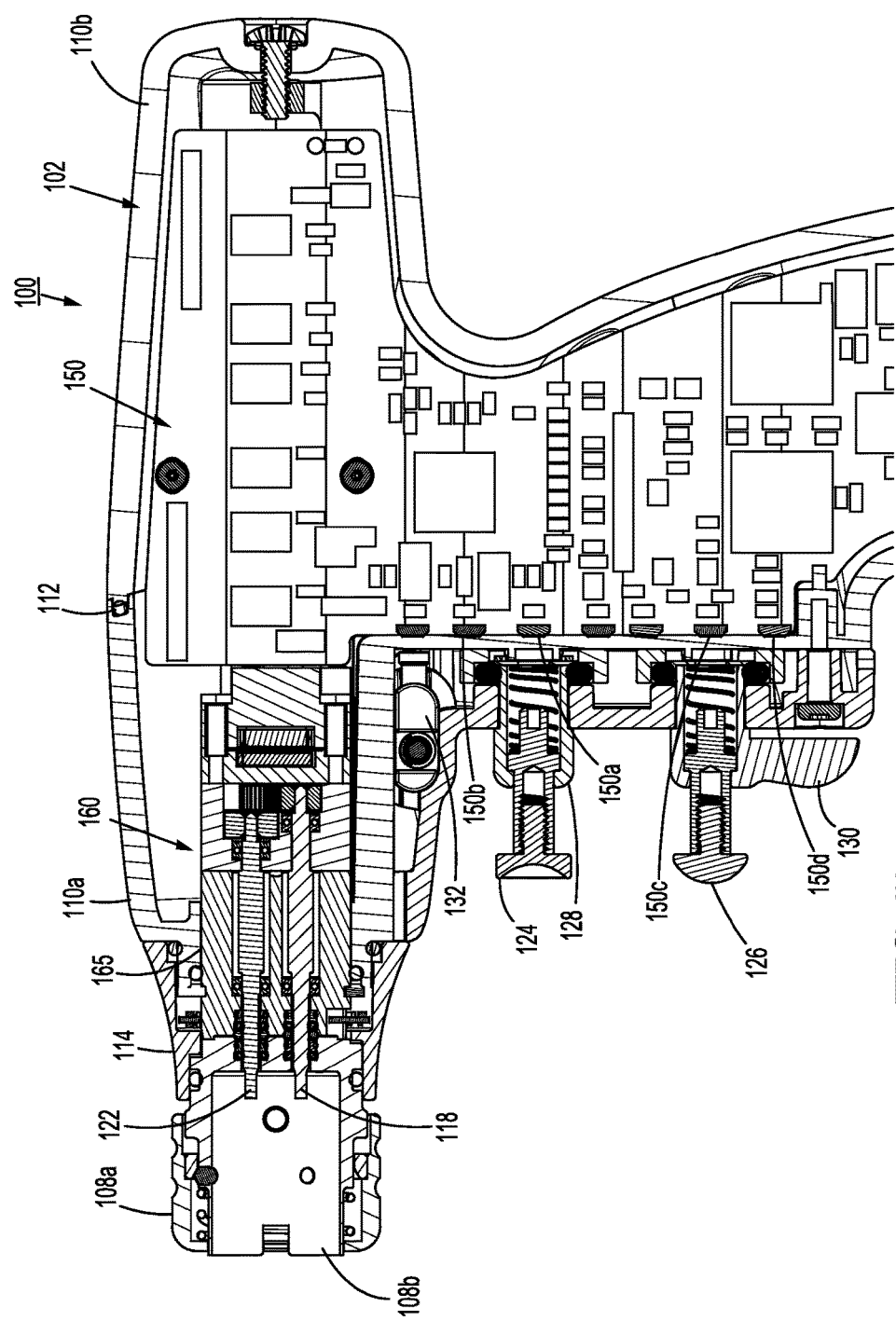
FIG. 7 is a side, cross-sectional view of the surgical instrument of FIG. 1, as taken through 7-7 of FIG. 2, according to the present disclosure.
Figure 8:
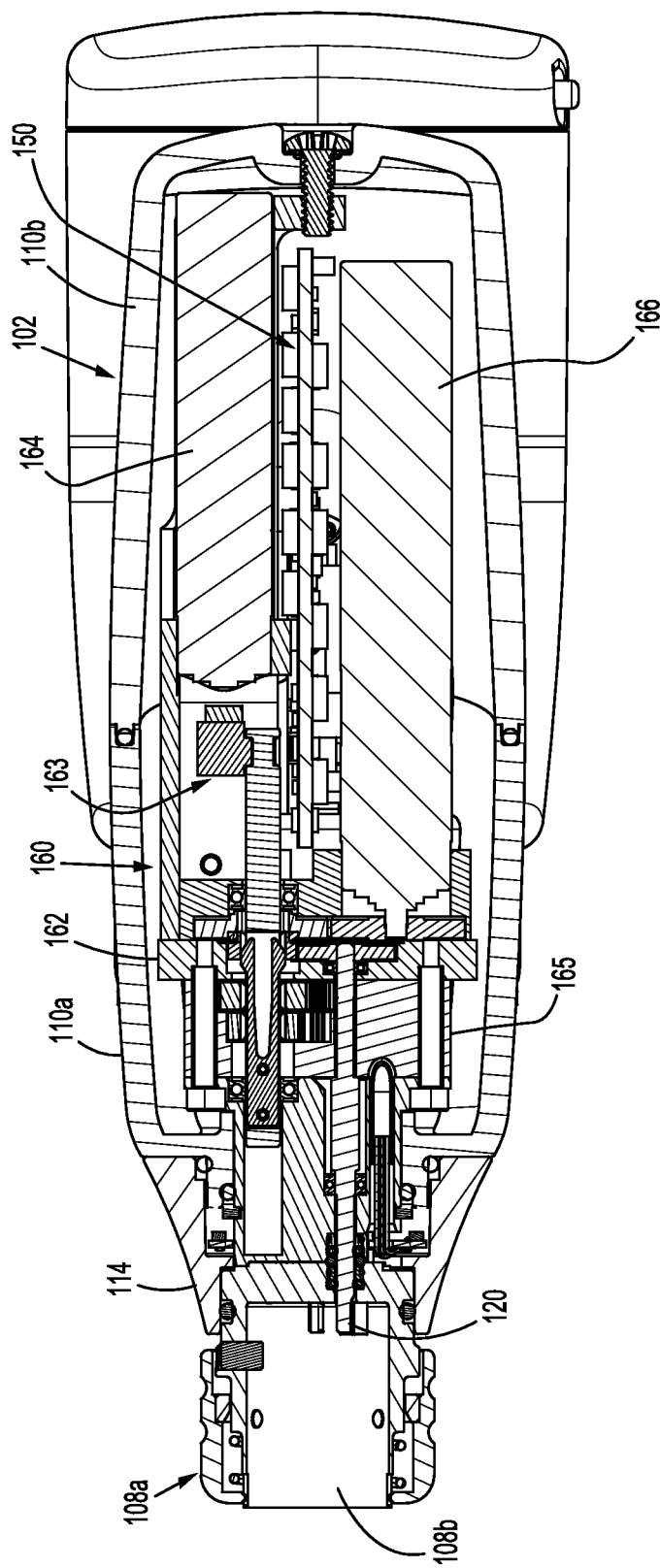
FIG. 8 is a top, cross-sectional view of the surgical instrument of FIG. 1, as taken through 8-8 of FIG. 2, according to the present disclosure.

As illustrated in FIGS. 6-8, connecting portion 108a of surgical instrument 100 has a cylindrical recess 108b that receives a drive coupling assembly 210 of adapter 200 when adapter 200 is mated to surgical instrument 100. Connecting portion 108a houses three rotatable drive connectors 118, 120, 122.

When adapter 200 is mated to surgical instrument 100, each of rotatable drive connectors 118, 120, 122 of surgical instrument 100 couples with a corresponding rotatable connector sleeve 218, 220, 222 of adapter 200, as shown in FIG. 6. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter 200.

The mating of drive connectors 118, 120, 122 of surgical instrument 100 with connector sleeves 218, 220, 222 of adapter 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160.

Since each of drive connectors 118, 120, 122 of surgical instrument 100 has a keyed and/or substantially non-rotatable interface with respective connector sleeves 218, 220, 222 of adapter 200, when adapter 200 is coupled to surgical instrument 100, rotational force(s) are selectively transferred from drive mechanism 160 of surgical instrument 100 to adapter 200.

The selective rotation of drive connector(s) 118, 120 and/or 122 of surgical instrument 100 allows surgical instrument 100 to selectively actuate different functions of end effector 300. As will be discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 transverse to longitudinal axis "X" (see FIG. 2). Additionally, the selective and independent rotation of third drive connector 122 of surgical instrument 100 corresponds to the selective and independent rotation of end effector 300 about longitudinal axis "X" (see FIG. 2) relative to handle housing 102 of surgical instrument 100.

As mentioned above and as illustrated in FIGS. 5 and 8, drive mechanism 160 includes a selector gearbox assembly 162; and a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical instrument 100 at a given time.

As illustrated in FIGS. 1-3, handle housing 102 supports a control assembly 107 on a distal surface or side of intermediate housing portion 108. The control assembly 107 is a fully-functional mechanical subassembly that can be assembled and tested separately from the rest of the instrument 100 prior to coupling thereto.

Control assembly 107, in cooperation with intermediate housing portion 108, supports a pair of finger-actuated control buttons 124, 126 and a pair rocker devices 128, 130 within a housing 107a. The control buttons 124, 126 are coupled to extension shafts 125, 127 respectively. In particular, control assembly 107 defines an upper aperture 124a for slidably receiving the extension shaft 125, and a lower aperture 126a for slidably receiving the extension shaft 127.

As seen in FIGS. 1, 2 and 7, surgical instrument 100 includes a fire button or safety switch 132 supported between intermediate housing portion 108 and upper housing portion, and situated above trigger housing 107. In use, tool assembly 304 of end effector 300 is actuated between opened and closed conditions as needed and/or desired. In order to fire end effector 300, to expel fasteners therefrom when tool assembly 304 of end effector 300 is in a closed condition, safety switch 132 is depressed thereby instructing surgical device 100 that end effector 300 is ready to expel fasteners therefrom.

Reference may be made to U.S. Provisional Patent Application Ser. No. 61/654,191, filed on Jun. 1, 2012, entitled "Hand Held Surgical Handle Assembly, Surgical Adapters for Use Between Surgical Handle Assembly and Surgical End Effectors, and Methods of Use," the entire content of which is incorporated herein by reference, for a detailed discussion of the construction and operation of features and components of surgical instrument 100 that are not explicitly described herein.

Figure 9:
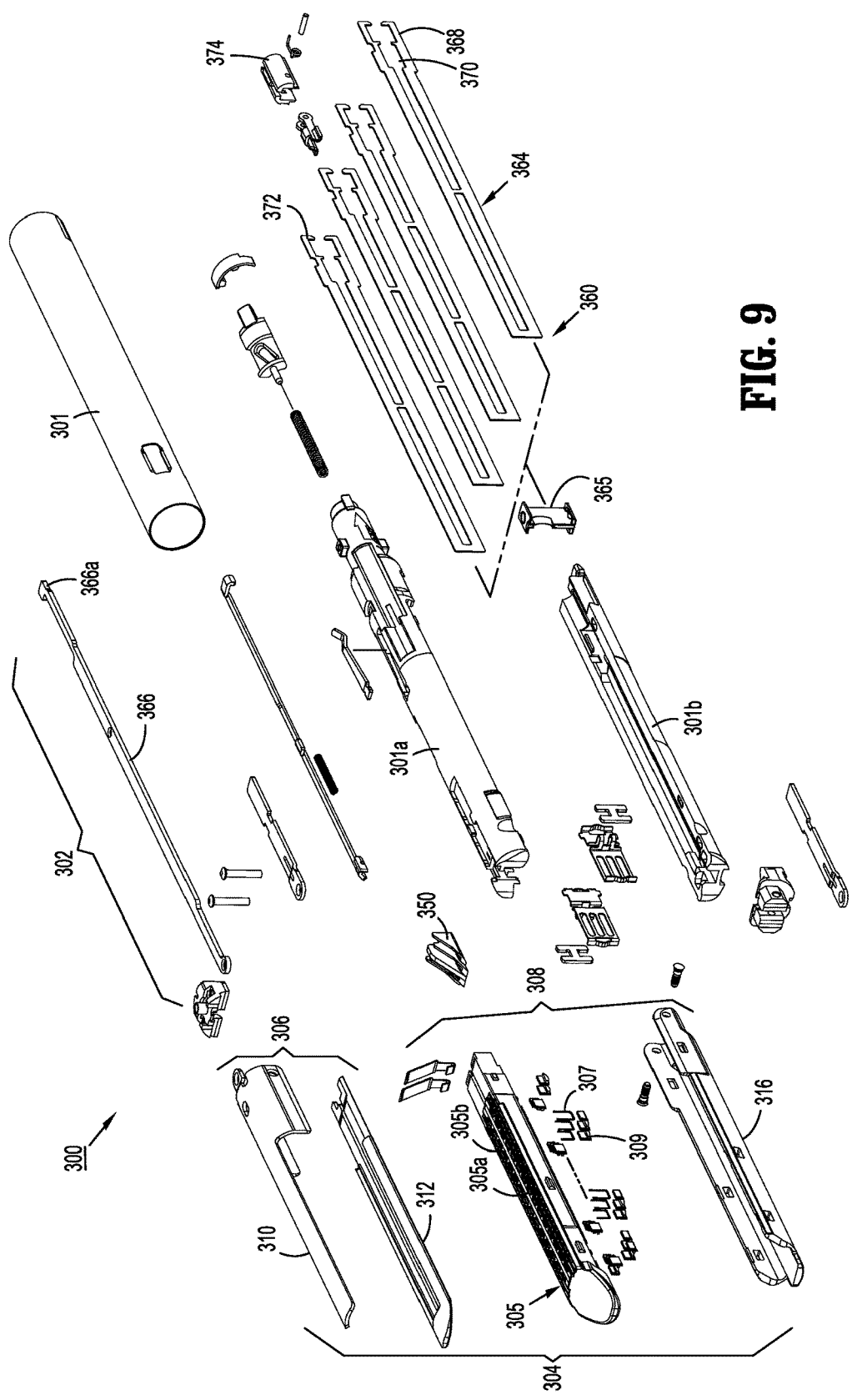
FIG. 9 is a perspective, exploded view of a end effector of FIG. 1, according to the present disclosure.

Referring to FIG. 9, drive assembly 360 of end effector 300 includes a flexible drive shaft 364 having a distal end which is secured to a dynamic drive beam 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of shaft 364. Drive member 374 defines a proximal porthole which receives a connection member of drive tube 246 (FIG. 1) of adapter 200 when end effector 300 is attached to distal coupling 230 of adapter 200.

When drive assembly 360 is advanced distally within tool assembly 304, an upper beam of drive beam 365 moves within a channel defined between anvil plate 312 and anvil cover 310 and a lower beam moves within a channel of the staple cartridge 305 and over the exterior surface of carrier 316 to close tool assembly 304 and fire staples therefrom.

Proximal body portion 302 of end effector 300 includes a sheath or outer tube 301 enclosing an upper housing portion 301a and a lower housing portion 301b. The housing portions 301a and 301b enclose an articulation link 366 having a hooked proximal end 366a which extends from a proximal end of end effector 300. Hooked proximal end 366a of articulation link 366 engages a coupling hook (not shown) of adapter 200 when end effector 300 is secured to distal housing 232 of adapter 200. When drive bar (not shown) of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 9, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of instrument 100, drive assembly 360 abuts an actuation sled 350 and pushes actuation sled 350 through cartridge 305. As the actuation sled moves through cartridge 305, cam wedges of the actuation sled 350 sequentially engage staple pushers 309 to move staple pushers 309 vertically within staple retention slots 305b and sequentially eject a single staple 307 therefrom for formation against anvil plate 312.

The end effector 300 may also include one or more mechanical lockout mechanisms, such as those described in commonly-owned U.S. Pat. Nos. 5,071,052; 5,397,046; 5,413,267; 5,415,335; 5,715,988; 5,718,359; and 6,109,500, the entire contents of all of which are incorporated by reference herein. Reference may also be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of end effector 300.

Figure 10:
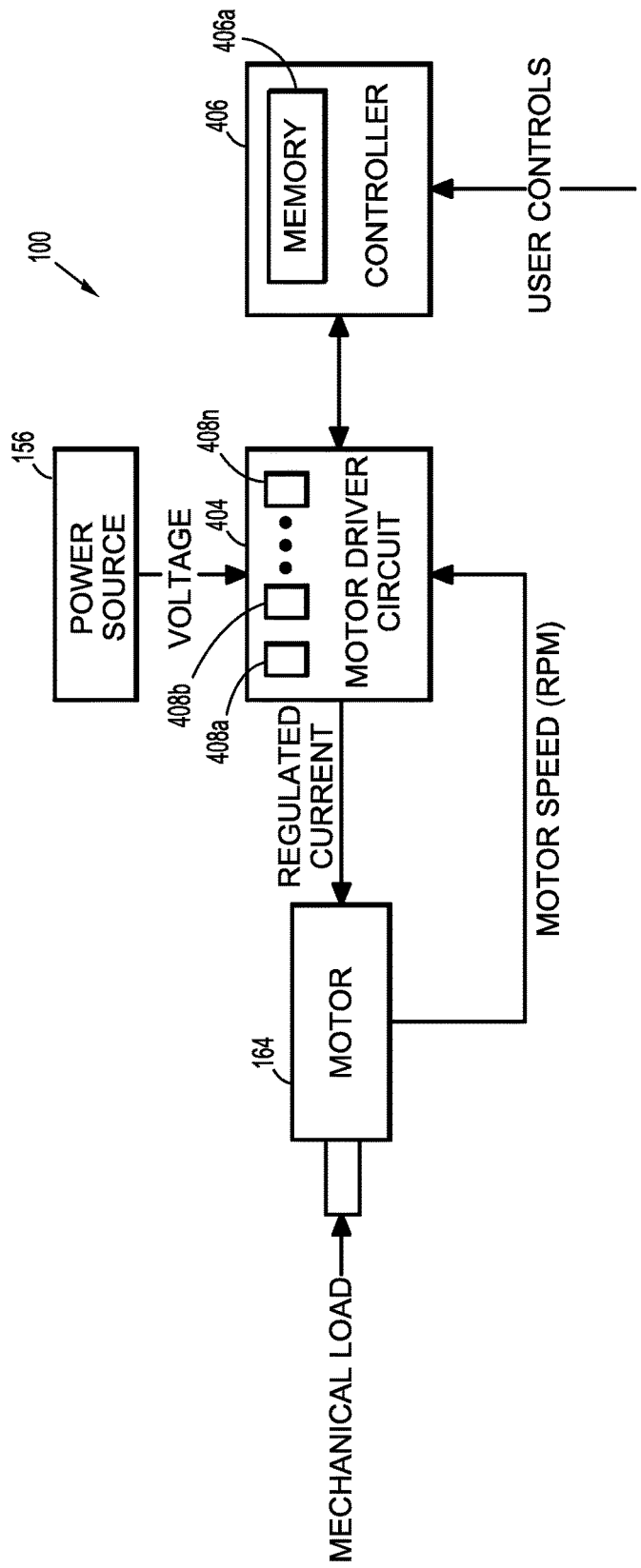
FIG. 10 is a schematic diagram of the surgical instrument of FIG. 1 according to the present disclosure.

Another embodiment of the instrument 100 is shown in FIG. 10. The instrument 100 includes the motor 164. The motor 164 may be any electrical motor configured to actuate one or more drives (e.g., rotatable drive connectors 118, 120, 122 of FIG. 6). The motor 164 is coupled to the battery 156, which may be a DC battery (e.g., rechargeable lead-based, nickel-based, lithium-ion based, battery etc.), an AC/DC transformer, or any other power source suitable for providing electrical energy to the motor 164.

The battery 156 and the motor 164 are coupled to a motor driver circuit 404 disposed on the circuit board 154 which controls the operation of the motor 164 including the flow of electrical energy from the battery 156 to the motor 164. The instrument 100 may use multiple motors 164 and motor driver circuits 404 or a transmission associated with a motor 100 (all not shown) to drive various functions of the instrument. The driver circuit 404 includes a plurality of sensors 408a, 408b, 408n configured to measure operational states of the motor 164 and the battery 156. The sensors 408a-n may include voltage sensors, current sensors, temperature sensors, telemetry sensors, optical sensors, and combinations thereof. The sensors 408a-408n may measure voltage, current, and other electrical properties of the electrical energy supplied by the battery 156. The sensors 408a-408n may also measure rotational speed as revolutions per minute (RPM), torque, temperature, current draw, and other operational properties of the motor 164. RPM may be determined by measuring the rotation of the motor 164. Position of various drive shafts (e.g., rotatable drive connectors 118, 120, 122 of FIG. 6) may be determined by using various linear sensors disposed in or in proximity to the shafts or extrapolated from the RPM measurements. In embodiments, torque may be calculated based on the regulated current draw of the motor 164 at a constant RPM. In further embodiments, the driver circuit 404 and/or the controller 406 may measure time and process the above-described values as a function thereof, including integration and/or differentiation, e.g., to determine the change in the measured values and the like.

The driver circuit 404 is also coupled to a controller 406, which may be any suitable logic control circuit adapted to perform the calculations and/or operate according to a set of instructions described in further detail below. The controller 406 may include a central processing unit operably connected to a memory which may include transitory type memory (e.g., RAM) and/or non-transitory type memory (e.g., flash media, disk media, etc.). The controller 406 includes a plurality of inputs and outputs for interfacing with the driver circuit 404. In particular, the controller 406 receives measured sensor signals from the driver circuit 404 regarding operational status of the motor 164 and the battery 156 and, in turn, outputs control signals to the driver circuit 404 to control the operation of the motor 164 based on the sensor readings and specific algorithm instructions, which are discussed in more detail below. The controller 406 is also configured to accept a plurality of user inputs from a user interface (e.g., switches, buttons, touch screen, etc. of the control assembly 107 coupled to the controller 406).

The present disclosure provides for an apparatus and method for controlling the instrument 100 or any other powered surgical instrument, including, but not limited to, linear powered staplers, circular or arcuate powered staplers, clip appliers, graspers, electrosurgical sealing forceps, rotary tissue blending devices, and the like.

Specifically, according to the present disclosure, algorithms are provided for controlling surgical instrument 100 and/or surgical system 10 in the event that an input element (i.e., control buttons 124, 126, rocker devices 128, 130, other buttons, switches, touch screens, controls, toggles, etc.) should malfunction or otherwise become inoperable or non-responsive during a surgical procedure, i.e., following initial actuation of surgical instrument 100 and/or surgical system 10. In such a situation, it is imperative that surgical instrument 100 and/or surgical system 10 be provided with an emergency retraction algorithm to overcome any malfunction, inoperability or non-responsiveness of any input element of surgical instrument 100 and/or surgical system 10.

Figure 11:
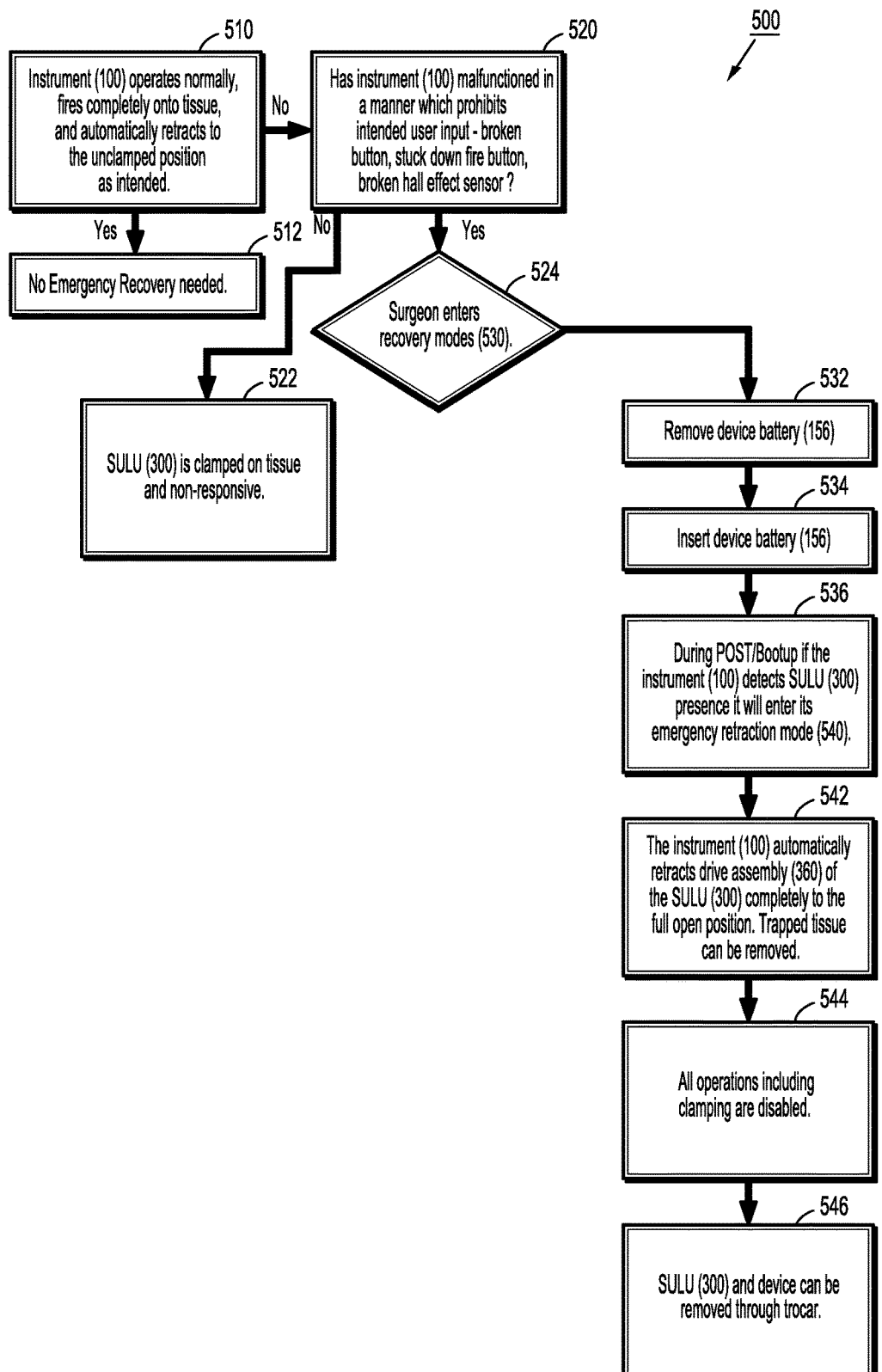
FIG. 11 is a flow chart of an emergency retraction algorithm for the electromechanical surgical system, according to an embodiment of the present disclosure.

As seen in FIG. 11, a flow chart of an algorithm, in accordance with a first aspect of the present disclosure, is generally designated as 500. Computer code or instructions implementing algorithm 500 may be retained locally in circuit board 150 or circuit board 154 of surgical instrument 100, in a memory device (not shown) of end effector 300, or in a remote computer system (not shown) which is in wired or wireless communication with surgical instrument 100 and/or surgical system 10.

In use, during operation of surgical system 10, sensors and the like monitor the operation of surgical instrument 100 and/or end effector 300. As seen in the flow chart of FIG. 11, if, at step 510, surgical instrument 100 operates normally (i.e., end effector 300 fires completely into tissue, and end effector 300 automatically retracts an unclamped position), as intended, then, at step 512, an emergency recovery mode 530 is not executed.

However, if, at step 510, surgical instrument 100 fails to operate normally or as intended, then, at step 520, an inquiry is executed related to a functionality of the input elements discussed above. If, at step 520, it is determined that surgical instrument 100 has not malfunctioned in a manner which prohibits intended user actuation of the input elements (i.e., broken button, stuck down fire button, broken hall effect sensor, etc.), then, at step 522, it is concluded that end effector 300 is clamped onto underlying tissue and nonresponsive, requiring further intervention.

If, at step 520, it is determined that surgical instrument 100 has malfunctioned in a manner which prohibits intended user actuation of the input elements, then, at step 524, the surgeon enters emergency recovery mode 530.

Emergency recovery mode 530 includes at least the following steps. At step 532, the surgeon removes battery 156 from lower housing portion of handle housing 102 of surgical instrument 100. Then, at step 534, re-insert battery 156 into lower housing portion of handle housing 102 of surgical instrument 100. After re-insertion of battery 156 into surgical instrument 100, at step 536, surgical instrument 100 undergoes a re-boot or boot-up sequence.

Since end effector 300 and adapter 200 are still attached or connected to surgical instrument 100, during the re-boot or boot-up sequence, at step 536, surgical instrument 100 detects the presence of end effector 300 and enters an emergency retraction mode 540.

This simple removal and insertion of battery 156 by the surgeon, and its automatic undergoing of a re-boot or boot-up sequence, may be considered an "intuitive activation." The "intuitive activation" to enter the emergency retraction mode 540 may be achieved even with a maximum degree of damage to surgical instrument (i.e., all input elements damaged and only battery connections, main circuit board 150 and the drive train of surgical system 10 are functioning).

While in the emergency retraction mode 540, at step 542, instrument 100 automatically fully retracts drive assembly 360 of end effector 300 by setting function selection module 163 to operate an appropriate one of drive connectors 118, 120, 122 (i.e., first drive connector 118 which is associated with the opening and closing of tool assembly 304 of end effector 300), and activating second motor 166 in reverse. Drive assembly 360 of end effector 300 is retracted until tool assembly 304 of end effector 300 is returned to a fully open position. With tool assembly 304 of end effector 300 in a fully open position, any tissue trapped within tool assembly 304 may be removed.

Then, either prior to, simultaneously with, or immediately following removal of the trapped tissue from tool assembly 304 of end effector 300, at step 544, all remaining operations or functions of surgical instrument 100 (i.e., including clamping and/or firing) are disabled. Then, at step 546, surgical instrument 100, adapter 200 and/or end effector 300 is/are removed from the surgical site (i.e., withdrawn from the trocar or the like).

Figure 12:
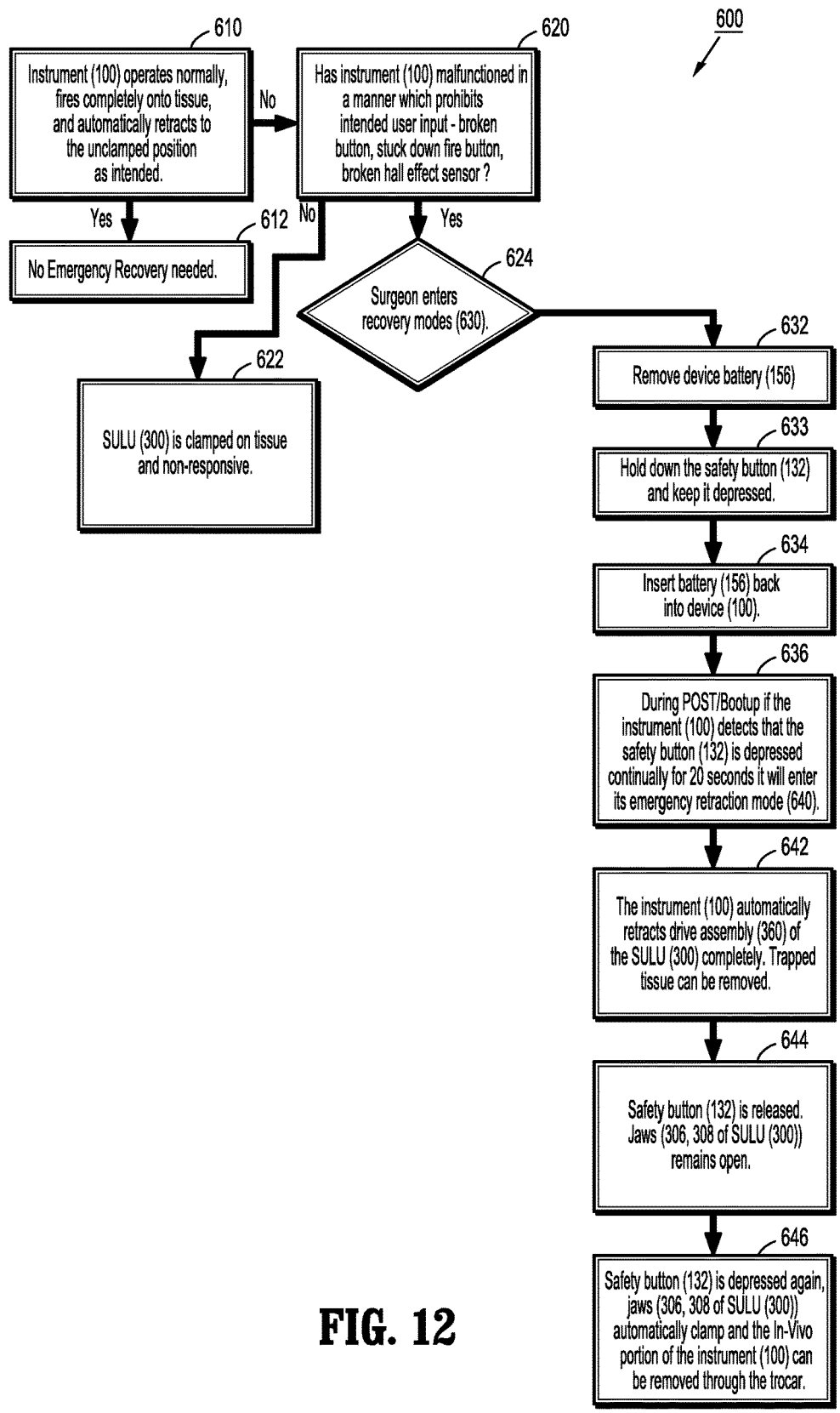
FIG. 12 is a flow chart of an emergency retraction algorithm for the electromechanical surgical system, according to another embodiment of the present disclosure.

As seen in FIG. 12, a flow chart of an algorithm, in accordance with a second aspect of the present disclosure, is generally designated as 600. Algorithm 600 may be retained locally in circuit board 150 or circuit board 154 of surgical instrument 100, in a memory device (not shown) of end effector 300, or in a remote computer system (not shown) which is in wired or wireless communication with surgical instrument 100 and/or surgical system 10.

In use, during operation of surgical system 10, sensors and the like monitor the operation of surgical instrument 100 and/or end effector 300. As seen in the flow chart of FIG. 12, if, at step 610, surgical instrument 100 operates normally (i.e., end effector 300 fires completely into tissue, and end effector 300 automatically retracts an unclamped position), as intended, then, at step 612, an emergency recovery mode 630 is not executed.

However, if, at step 610, surgical instrument 100 fails to operate normally or as intended, then, at step 620, an inquiry is executed related to a functionality of the input elements discussed above. If, at step 620, it is determined that surgical instrument 100 has not malfunctioned in a manner which prohibits intended user actuation of the input elements (i.e., broken button, stuck down fire button, broken hall effect sensor, etc.), then, at step 622, it is concluded that end effector 300 is clamped onto underlying tissue and nonresponsive.

If, at step 620, it is determined that surgical instrument 100 has malfunctioned in a manner which prohibits intended user actuation of the input elements, then, at step 624, the surgeon enters emergency recovery mode 630.

Emergency recovery mode 630 includes at least the following steps. At step 632, the surgeon removes battery 156 from lower housing portion of handle housing 102 of surgical instrument 100. Then, at step 633, the surgeon depresses and holds down safety button 132 of surgical instrument 100. With safety button 132 depressed and held down, then, at step 634, the surgeon re-inserts battery 156 into lower housing portion of handle housing 102 of surgical instrument 100. After re-insertion of battery 156 into surgical instrument 100, at step 636, surgical instrument 100 undergoes a re-boot or boot-up sequence.

Since safety button 132 has been continuously depressed or held down (i.e., for between about 0 and 30 seconds, desirably about 20 seconds) while battery 156 is re-inserted, during the re-boot or boot-up sequence, at step 636, surgical instrument 100 detects that safety button 132 has been so depressed or held and enters an emergency retraction mode 640.

While in the emergency retraction mode 640, at step 642, instrument 100 automatically fully retracts drive assembly 360 of end effector 300 by setting function selection module 163 to operate an appropriate one of drive connectors 118, 120, 122 (i.e., first drive connector 118 which is associated with the opening and closing of tool assembly 304 of end effector 300), and activating second motor 166 in reverse. Drive assembly 360 of end effector 300 is retracted until tool assembly 304 of end effector 300 is returned to a fully open position. With tool assembly 304 of end effector 300 in a fully open position, any tissue trapped within tool assembly 304 may be removed.

Then, either prior to, simultaneously with, or immediately following removal of the trapped tissue from tool assembly 304 of end effector 300, at step 644, safety button 132 is released, and jaws 306, 308 of end effector 300 remain open.

Then, at step 646, safety button 132 is re-depressed or re-held down, jaws 306, 308 of end effector 300 are automatically re-actuated to a closed or clamped position, to re-clamp onto the tissue, whereby the "in vivo" or re-clamped tissue may be removed from the surgical site (i.e., withdrawn from the trocar or the like).

In the present aspect of the disclosure, the user or surgeon controls the activation of the emergency retraction mode 640 by depressing and holding down safety button 132 for a specified period of time. In accordance with the present disclosure, in an alternate arrangement or set-up, input elements (i.e., control buttons 124, 126; rocker devices 128, 130; etc.) other than safety button 132 may be depressed and held down for a specified period of time during the re-boot or boot-up sequence in order for surgical system 10 and/or surgical instrument 100 to enter the emergency retraction mode 640.

Additionally, in accordance with the present aspect of the disclosure, functionality of surgical system 10 and/or surgical instrument 100, when surgical system 10 and/or surgical instrument 100 is in the emergency retraction mode 640, is limited solely to the closure of jaws 306, 308 of end effector 300.

Figure 13:
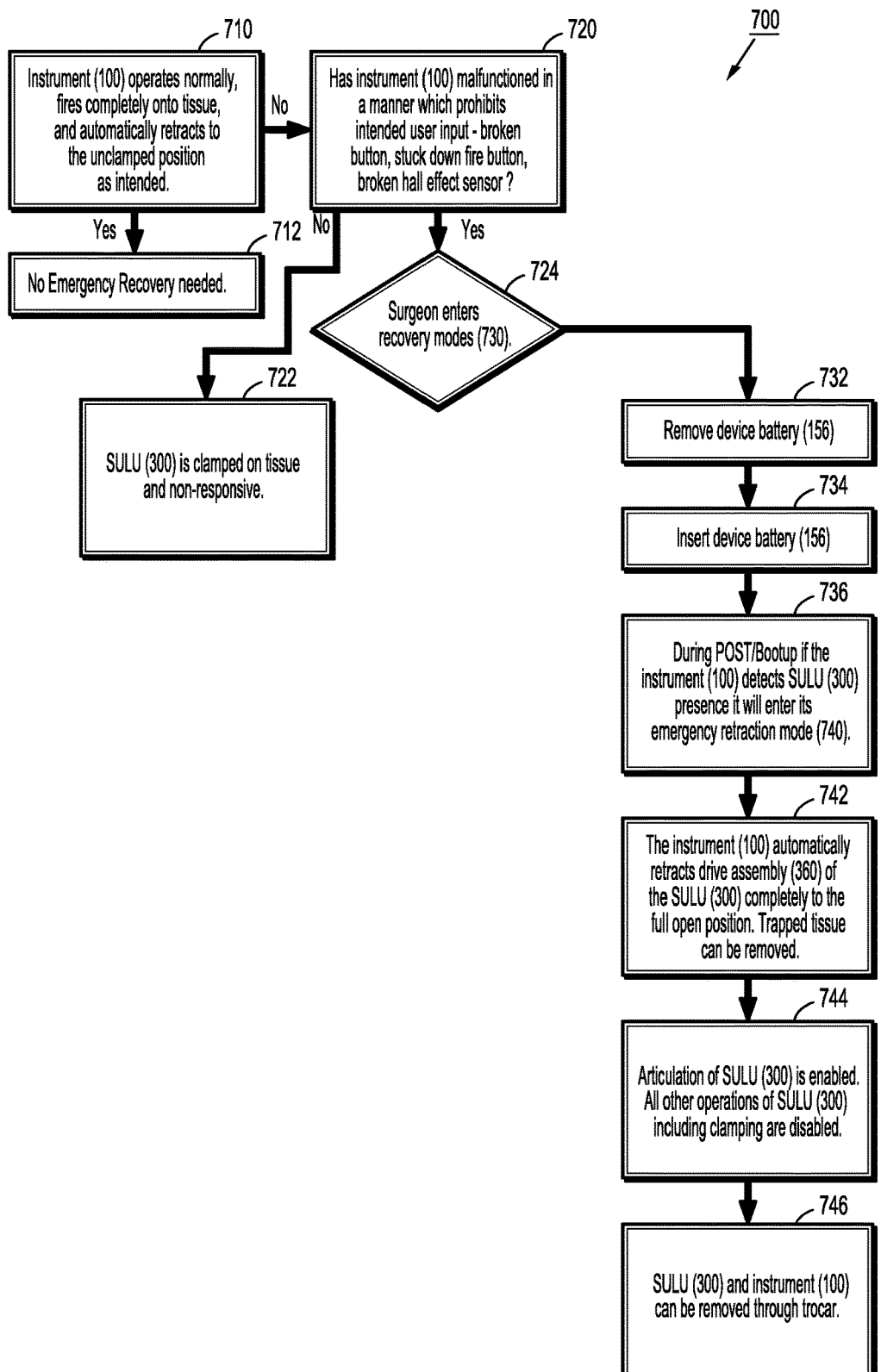
FIG. 13 is a flow chart of an emergency retraction algorithm for the electromechanical surgical system, according to yet another embodiment of the present disclosure.

As seen in FIG. 13, a flow chart of an algorithm, in accordance with yet another aspect of the present disclosure, is generally designated as 700. Algorithm 700 may be retained locally in circuit board 150 or circuit board 154 of surgical instrument 100, in a memory device (not shown) of end effector 300, or in a remote computer system (not shown) which is in wired or wireless communication with surgical instrument 100 and/or surgical system 10.

In use, during operation of surgical system 10, sensors and the like monitor the operation of surgical instrument 100 and/or end effector 300. As seen in the flow chart of FIG. 13, if, at step 710, surgical instrument 100 operates normally (i.e., end effector 300 fires completely into tissue, and end effector 300 automatically retracts an unclamped position), as intended, then, at step 712, an emergency recovery mode 730 is not executed.

However, if, at step 710, surgical instrument 100 fails to operate normally or as intended, then, at step 720, an inquiry is executed related to a functionality of the input elements discussed above. If, at step 720, it is determined that surgical instrument 100 has not malfunctioned in a manner which prohibits intended user actuation of the input elements (i.e., broken button, stuck down fire button, broken hall effect sensor, etc.), then, at step 722, it is concluded that end effector is clamped onto underlying tissue and nonresponsive.

If, at step 720, it is determined that surgical instrument 100 has malfunctioned in a manner which prohibits intended user actuation of the input elements, then, at step 724, the surgeon enters emergency recovery mode 730.

Emergency recovery mode 730 includes at least the following steps. At step 732, the surgeon removes battery 156 from lower housing portion of handle housing 102 of surgical instrument 100. Then, at step 734, re-insert battery 156 into lower housing portion of handle housing 102 of surgical instrument 100. After re-insertion of battery 156 into surgical instrument 100, at step 736, surgical instrument 100 undergoes a re-boot or boot-up sequence.

Since end effector 300 and adapter 200 are still attached or connected to surgical instrument 100, during the re-boot or boot-up sequence, at step 736, surgical instrument 100 detects the presence of end effector 300 and enters an emergency retraction mode 740.

This simple removal and insertion of battery 156 by the surgeon, and its automatic undergoing of a re-boot or boot-up sequence, may be considered an "intuitive activation." The "intuitive activation" to enter the emergency retraction mode 740 may be achieved even with a maximum degree of damage to surgical instrument (i.e., all input elements damaged and only battery connections, main circuit board 150 and the drive train of surgical system 10 are functioning).

While in the emergency retraction mode 740, at step 742, instrument 100 automatically fully retracts drive assembly 360 of end effector 300 by setting function selection module 163 to operate an appropriate one of drive connectors 118, 120, 122 (i.e., first drive connector 118 which is associated with the opening and closing of tool assembly 304 of end effector 300), and activating second motor 166 in reverse. Drive assembly 360 of end effector 300 is retracted until tool assembly 304 of end effector 300 is returned to a fully open position. With tool assembly 304 of end effector 300 in a fully open position, any tissue trapped within tool assembly 304 may be removed.

Then, either prior to, simultaneously with, or immediately following removal of the trapped tissue from tool assembly 304 of end effector 300, at step 744, all operations or functions of surgical instrument 100 (i.e., including clamping and/or firing) are disabled, except for an articulation function of end effector 300. Then, at step 746, surgical instrument 100, adapter 200 and/or end effector 300 is/are removed from the surgical site (i.e., withdrawn from the trocar or the like).

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

It should be further understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A method for controlling an electromechanical surgical system that includes a hand-held surgical instrument selectively and removably supporting an end effector, wherein the surgical instrument includes a motor, a controller in electrical communication with the motor, a battery in electrical communication with at least one of the motor and the controller, and at least one input element actuatable by a user to send control signals to the controller to operate the motor; and wherein the end effector includes a jaw assembly, a drive assembly at least partially located within the jaw assembly and operatively connectable to the motor when the end effector is connected to the surgical instrument for actuation by the motor, the method comprising:

monitoring the at least one input element;
removing the battery from the surgical instrument;
re-inserting the battery into the surgical instrument;
entering an emergency retraction mode in response to the removal and re-insertion of the battery into the surgical instrument; and
activating the motor during the emergency retraction mode to withdraw the drive assembly from any advanced position thereof.

2. The method according to claim 1, further comprising:
detecting, by the controller, that the end effector is connected to the surgical instrument, and
wherein the emergency retraction mode includes re-booting the controller.

3. The method according to claim 2, wherein entering the emergency retraction mode includes automatically retracting the drive assembly.

4. The method according to claim 3, further comprising opening the jaw assembly concomitantly with the retraction of the drive assembly to a fully retracted position.

5. The method according to claim 1, wherein entering the emergency retraction mode includes:
pressing and holding of a safety button supported on the surgical instrument prior to re-insertion of the battery into the surgical instrument.

6. The method according to claim 5, further comprising:
detecting, by the controller, that the end effector is connected to the surgical instrument, and
wherein the emergency retraction mode includes re-booting the controller.

7. The method according to claim 6, wherein the emergency retraction mode includes automatically retracting the drive assembly.

8. The method according to claim 7, further comprising opening the jaw assembly concomitantly with the retraction of the drive assembly to a fully retracted position.

9. The method according to claim 7, further comprising following retraction of the drive assembly, and following a release of the safety button, the controller awaits user input prior to advancing the drive assembly.

10. The method according to claim 9, wherein the emergency retraction mode includes reclosing the jaw assembly following a release of the safety button and re-pressing and holding of the safety button.

11. The method according to claim 1, wherein the emergency retraction mode includes articulating the end effector.

12. The method according to claim 1, wherein the emergency retraction mode includes re-booting the controller.

13. The method according to claim 12, further comprising detecting, by the controller, that the end effector is connected to the surgical instrument.

14. The method according to claim 13, wherein the emergency retraction mode includes automatically retracting the drive assembly.

15. The method according to claim 1, further comprising:
entering the emergency retraction mode upon the removal of the battery from the surgical instrument;
pressing and holding of a safety button that is supported on the surgical instrument prior to re-insertion of the battery into the surgical instrument.

16. The method according to claim 15, further comprising:
re-booting the controller during the emergency retraction mode; and
detecting, by the controller, that the end effector is connected to the surgical instrument.

17. The method according to claim 16, wherein the emergency retraction mode includes:
  automatically retracting the drive assembly; and
  opening the jaw assembly to a fully retracted position.

* * * * *